United States Patent [19]

Rose et al.

[11] Patent Number: 5,407,678
[45] Date of Patent: Apr. 18, 1995

[54] PETROLEUM JELLY CREAM

[75] Inventors: Walter Rose, New Haven; Amy C. Zimmerman, Ansonia, both of Conn.

[73] Assignee: Chesebrough-Pond's USA Co., Division of Conopco, Inc., Greenwich, Conn.

[21] Appl. No.: 115,490

[22] Filed: Sep. 1, 1993

[51] Int. Cl.$^6$ ............................................. A61K 7/00
[52] U.S. Cl. .................................... 424/401; 514/844
[58] Field of Search ......................... 424/401; 514/844

[56] References Cited

U.S. PATENT DOCUMENTS

| | | | |
|---|---|---|---|
| 3,852,475 | 12/1974 | Tarangul | 424/401 |
| 4,981,845 | 1/1991 | Pereira | 514/557 |
| 5,013,763 | 5/1991 | Tubesing et al. | 514/772 |
| 5,106,838 | 4/1992 | Reinhart | 514/59 |

FOREIGN PATENT DOCUMENTS 0262681 4/1988 European Pat. Off.
0295411 12/1988 European Pat. Off.

OTHER PUBLICATIONS

PCT International Search Report.

*Primary Examiner*—Thurman K. Page
*Assistant Examiner*—Amy Hulina
*Attorney, Agent, or Firm*—Milton L. Honig

[57] ABSTRACT

A cosmetic composition is described that includes an aqueous combination of petroleum jelly, aluminum starch octenylsuccinate and a $C_{12}$–$C_{15}$ alkyl lactate. The composition provides petroleum jelly in a nongreasy but efficacious form to counteract skin dryness.

6 Claims, No Drawings

PETROLEUM JELLY CREAM

BACKGROUND OF THE INVENTION

1. Field of the Invention

The invention relates to a cosmetic emulsion based upon petroleum jelly.

2. The Related Art

Petroleum jelly is one of the oldest skin treatment products still in commerce today. For over 100 years, the Chesebrough Company and its successors have sold this substance under the brand, Vaseline ®. There is good reason for the longevity of this product. Its occlusive and healing properties render this product especially efficacious against dry and damaged skin.

If petroleum jelly has any drawbacks, it undoubtedly involves the greasy nature of the substance. Petroleum jelly can rub off on clothes or anything else in contact therewith. Thus, the art has sought a product with the benefits of petroleum jelly but lacking its disadvantages.

Accordingly, it is an object of the present invention to provide a cosmetic composition with a substantial amount of petrolum jelly that, nevertheless, is relatively nongreasy.

Another object of the present invention is to provide a cosmetic composition based upon petroleum jelly in the form of a creamy emulsion that provides essentially the same moisturizing, protecting and restoring properties against dry skin as would 100% petroleum jelly.

Still another object of the present invention is to provide a cosmetic composition based upon petroleum jelly that is an emulsion with good phase stability and pleasing aesthetics.

These and other objects of the present invention will more fully be appreciated through the detailed description that follows.

SUMMARY OF THE INVENTION

A cosmetic composition is provided that includes:
(i) from 30 to 95% by weight of petrolum jelly;
(ii) from 10 to 65% by weight of water;
(iii) from 1 to 10% by weight of aluminum starch octenylsuccinate; and
(iv) from 0.1 to 10% by weight of $C_{12}$–$C_{15}$ alkyl lactate.

DETAILED DESCRIPTION

Now it has been discovered that a combination of aluminum starch octenylsuccinate and an alkyl lactate can combine with an aqueous emulsion of petroleum jelly to obtain a nongreasy skin protective product.

Accordingly, the main hydrophobic component of the composition will be petroleum jelly. This substance will be present in an amount from at least 30% up to 95%, preferably between about 30 and 50% by weight.

Water will be present in an amount from about 10 to 65%, preferably from about 45 to 65% by weight.

Essential to the invention of removing the greasy aspect of petroleum jelly is the presence of aluminum starch octenylsuccinate, available under the trademark Dry-Flo ® from the National Starch and Chemical Company, Bridgewater, N.J., The amount of this material may range from 1 to 10% by weight, optimally from 3.5 to 5% by weight.

A fourth essential component of cosmetic compositions according to the present invention is that of a $C_{12}$–$C_{15}$ alkyl lactate. Amounts of the lactate will range from 0.1 to 10%, preferably from 3 to 8%, optimally from 4 to 6% by weight. The alkyl lactate is necessary in conjunction with the aluminum starch octenylsuccinate to achieve an adequate gliding feel for the product on the skin.

When combining Dry-Flo ® into the cosmetic composition, it is preferable to add the material into the petroleum jelly and maintain the combination at a temperature between 38° C. and 100° C., preferably between 75° C. and 80° C. This heat treatment in the presence of water allows the Dry-Flo ® to undergo a controlled swelling which absorbs the petroleum jelly yielding the nongreasy effect.

Advantageously, cosmetic compositions of the present invention may also include a microcrystalline wax (in addition to any present naturally in the petroleum jelly). Amounts of the added microcrystalline wax may range from about 0.1 to 10%, preferably from 0.5 to 2%, optimally from 0.8 to 1.5% by weight. A preferred microcrystalline wax is Microwax 1275W/W 44 ®.

Beyond the aforementioned essential components, the cosmetic compositions of the present invention may also include other ingredients typically found in cosmetic formulations. Among these ingredients are emollients, solvents, humectants, thickeners, preservatives, fragrances and vitamins.

Emollients may be such materials as $C_8$–$C_{30}$ fatty alcohols, $C_8$–$C_{30}$ fatty acids, triglyceride oils, silicone oils and a variety of esters. Illustrative are stearyl alcohol, cetyl alcohol, stearic acid, isopropyl palmitate, isopropyl myristate, lanolin, sunflower oil, evening primrose oil, soybean oil, dimethyl polysiloxane and dimethyl polycyclosiloxane. Amounts of the emollient may range anywhere from about 0.5 to 20%. Most preferred is a mixture of stearyl alcohol and cetyl alcohol.

Solvents may include ethyl alcohol and isopropanol. Among the humectants may be included glycerin, diglycerin, sorbitol, ethylene glycol, polyethylene glycol, propylene glycol, polypropylene glycol and butylene glycol. Most preferred is a 1:1 mixture of glycerin and diglycerin.

Thickeners may be selected from such materials as crosslinked polyacrylates available under the Carbopol ® trademark, celluloses such as sodium carboxymethylcellulose, hydroxyethylcellulose, hydroxypropylcellulose and methyl cellulose, and natural gums such as xanthan, carrageenan and pectin gums. Most preferred are the crosslinked polyacrylates, especially Carbopol 934 ® available from the B. F. Goodrich Company.

Powders may be such materials as chalk, talc, Fullers earth, kaolin, starch, colloidal silica, smectites clays, montmorillonite clays and chemically modified magnesium aluminum silicates.

Among the preservatives useful are methyl paraben, propyl paraben, EDTA salts, potassium sorbate, potassium benzoate and DMDM hydantoin.

Cosmetic compositions of the present invention may also contain vitamin ingredients such as Vitamin A palmitate, Vitamin E acetate, Niacin, Vitamin C and combinations thereof.

Emulsifiers could also be useful for purposes of the present invention. These emulsifiers may be alkoxylated $C_8$–$C_{30}$ fatty acids and fatty alcohols. Examples of such materials are polyoxyethylene (4)lauryl ether, polyoxyethylene (8) monostearate, polyoxyethylene (10) cetyl ether and polyoxyethylene (20) stearyl ether. A particularly preferred emulsifier is Myreth-3-Myristate ®
available commercially as Cetiol 1414-E ®.

The following examples will more fully illustrate the embodiments of this invention. All parts, percentages and proportions referred to herein and in the appended claims are by weight of the total composition unless otherwise stated.

EXAMPLE 1

A cosmetic emulsion according to the present invention is outlined below.

| Component | Weight % |
| --- | --- |
| Petroleum Jelly | 30.0 |
| Carbopol 934 ® (2% soln.) | 15.0 |
| Dry-Flo ® | 5.0 |
| $C_{12}$–$C_{15}$ Alkyl Lactate | 5.0 |
| Cetiol 1414-E ® | 3.5 |
| Cetearyl Alcohol | 2.4 |
| Microwax 1275 ® | 1.0 |
| Glycerin | 1.0 |
| Diglycerin | 1.0 |
| Triethanolamine | 0.8 |
| Ethylene Brassylate | 0.15 |
| Glydant Plus ® | 0.1 |
| Vitamin E Acetate | 0.1 |
| Disodium EDTA | 0.05 |
| Water | Balance |

EXAMPLE 2

A further cosmetic emulsion according to the present invention is outlined below.

| Component | Weight % |
| --- | --- |
| Petroleum Jelly | 30.0 |
| Carbopol 934 ® (2% soln.) | 8.0 |
| Diethylene Glycol Dioctanoate | 5.0 |
| Dry-Flo ® | 5.0 |
| $C_{12}$–$C_{15}$ Alkyl Lactate | 3.5 |
| Cetiol 1414-E ® | 3.5 |
| Glycerin | 2.0 |
| Microwax 1275 ® | 1.0 |
| Triethanolamine | 0.6 |
| Glydant Plus ® | 0.1 |
| Disodium EDTA | 0.05 |
| Water | Balance |

EXAMPLE 3

A still further cosmetic emulsion according to the present invention is outlined below.

| Component | Weight % |
| --- | --- |
| Petroleum Jelly | 40.0 |
| Carbopol 934 ® (2% soln.) | 8.0 |
| Dry-Flo ® | 8.0 |
| $C_{12}$–$C_{15}$ Alkyl Lactate | 2.0 |
| Cetiol 1414-E ® | 1.5 |
| Cetearyl Alcohol | 1.3 |
| Microwax 1275 ® | 0.5 |
| Glycerin | 0.5 |
| Diglycerin | 0.5 |
| Triethanolamine | 0.4 |
| Ethylene Brassylate | 0.15 |
| Glydant Plus ® | 0.1 |
| Vitamin E Acetate | 0.1 |
| Disodium EDTA | 0.01 |
| Water | Balance |

The foregoing description and Examples illustrate selected embodiments of the present invention. In light thereof, various modifications will be suggested to one skilled in the art, all of which are within the spirit and purview of this invention.

What is claimed is:

1. A cosmetic composition comprising:
   (i) from 30 to 95% by weight of petroleum jelly;
   (ii) from 10 to 65% by weight of water;
   (iii) from 1 to 10% by weight of aluminum starch octenylsuccinate; and
   (iv) from 0.1 to 10% by weight of $C_{12}$–$C_{15}$ alkyl lactate.

2. A cosmetic composition according to claim 1 further comprising from 0.1 to 10% by weight of a microcrystalline wax in excess of any naturally present in the petroleum jelly.

3. A cosmetic composition according to claim 1 wherein the aluminum starch octenylsuccinate is present in an amount between 3.5 and 5% by weight.

4. A cosmetic composition according to claim 1 wherein the aluminum starch octenylsuccinate and petroleum jelly are combined together in forming the composition at a temperature between 38° C. and 100° C.

5. A cosmetic composition according to claim 1 wherein the petroleum jelly is present from 30 to 50% by weight.

6. A cosmetic composition according to claim 1 wherein the alkyl lactylate is present in an amount from 3 to 8% by weight.

* * * * *